United States Patent [19]
Bellin et al.

[11] Patent Number: 5,107,849
[45] Date of Patent: Apr. 28, 1992

[54] SYSTEM AND METHOD FOR CANCELLATION OF SIGNAL ARTIFACTS

[75] Inventors: Howard T. Bellin, New York; Robert P. Dingwall, Clinton Corners, both of N.Y.

[73] Assignee: Cortec, Inc., New York, N.Y.

[21] Appl. No.: 581,638

[22] Filed: Sep. 12, 1990

[51] Int. Cl.$^5$ .............................. A61B 5/0428
[52] U.S. Cl. ............................................ 128/696
[58] Field of Search ........................ 128/696, 702

[56] References Cited

U.S. PATENT DOCUMENTS

| | | | |
|---|---|---|---|
| 4,066,069 | 1/1978 | Dolch | 128/706 |
| 4,243,045 | 1/1981 | Maas | 128/696 |
| 4,381,786 | 5/1983 | Duggan | 128/696 |
| 4,408,615 | 10/1983 | Grossman | 128/696 |
| 4,478,224 | 10/1984 | Bailey | 128/706 |
| 4,630,612 | 12/1986 | Uchida et al. | 128/661.09 |
| 4,708,146 | 11/1987 | Lane | 128/723 |
| 4,936,309 | 6/1990 | Cooper | 128/706 |

Primary Examiner—William E. Kamm
Attorney, Agent, or Firm—Hopgood, Calimafde, Kalil, Blaustein & Judlowe

[57] ABSTRACT

A system for processing a repeating complex waveform that removes or reduces a significant portion of artifacts and other noise from the desired source signal. The system employs a phase detector for isolating artifacts from the source which are then used in processing the ECG waveform. The method and apparatus is especially useful in processing ECG signals reflective of heart conditions. The resulting clean signal makes accurate diagnosis of pending patient condition faster and more reliable.

12 Claims, 4 Drawing Sheets

SYSTEM AND METHOD FOR CANCELLATION OF SIGNAL ARTIFACTS

The present invention generally relates to a system for electrical signal enhancement, and more particularly, an apparatus and method for removing noise and artifacts from an electrical signal having a repeating complex waveform.

BACKGROUND OF THE INVENTION

A paramount concern in designing circuits for signal processing is the elimination or reduction of noise. Due to the broad diversity of desired source signals for processing and types of noise inherent thereto, a plethora of noise reduction systems have been developed. These prior art systems range from simple filters to program controlled signal enhancement computers. For the most part, these prior art noise reduction systems address the problem of reducing noise in a signal with a non-repeating waveform of significant complexity. An example would be an audio track from a tape source or LP. An audio signal source forms an essentially non-repeating waveform comprised of many different frequency components forming the desired signal and inherent noise. To reduce the noise content, circuits act to expand and compress segments of the audio signal, thereby selectively depressing those frequencies most poisoned by the noise. Unfortunately, this approach also depresses or eliminates portions of the source signal, thus reducing the quality of the output at the same time noise is removed.

There are important source signals that have a repeating complex waveform. For example, in the medical field, cardiologists are extremely interested in the electrical signals generated by the heart muscle during blood pumping operations. This signal is known as an electrocardiogram or "ECG" and has a repeating complex waveform associated with each beat of the heart. This complex waveform has undergone significant study by cardiologists. The waveform has been segmented into key portions for detailed study. It has been learned that various changes in the waveform are related to changes in the heart function. In fact, changes in certain segments of the waveform often act as a predictor to heart trouble, and therefore, are critical in diagnosis and prevention of heart disease.

The importance of ECG in the monitoring of the health of the heart cannot be overstated. Readings of the patient's ECG have now become a routine practice for the cardiologist, often taken right in his office. In this regard, the cardiologist will normally employ an oscilloscope or similar device for direct display of the ECG waveform, and ultimately a time graph printout. The cardiologist will review the ECG print-out looking for problems. The cardiologist may also compare the present ECG printout with a reading taken earlier. Differences in the two ECG signals often will indicate a health problem. For example, an elevated or depressed ST segment in the ECG reflects a certain type of heart valve disorder. The importance of the ST segment is more fully explained in U.S. Pat. No. 4,546,776 which is incorporated by reference herein in its entirety.

As noted in the above-referenced U.S. patent, the changes in the ECG waveform can be difficult to discern by the human eye. In addition, there are many potential sources of noise that further act to cloud the slight changes in the signal that are important in proper diagnosis. These noise sources include noise inherent in all electrical circuits, in addition to signal artifacts caused by patient movement, spurious electrical discharge unrelated to heart function, and sources in the doctor's office (e.g. fluorescent lights).

Noise induced artifacts in the ECG further inhibit a proper reading by the cardiologist causing erroneous diagnosis of life threatening conditions. It was with this understanding of the present problem the present invention was developed.

OBJECTS AND SUMMARY OF THE INVENTION

It is an object of the present invention to provide a system for removing or substantially reducing artifacts and other noise from a signal containing a repeating complex waveform.

It is another object of the present invention to provide an apparatus for reducing noise from a repeating signal without materially disturbing the complex waveform.

It is an additional object of the present invention to provide a method for reducing noise and other artifacts in an ECG signal.

It is yet another object of the present invention to provide a system for combining two or more complex waveforms taken at different times thereby isolating non-repeating noise and artifacts from the complex waveforms.

The above and other objects of the present invention are realized in a specific illustrative circuit which receives and divides an incoming ECG signal into at least two signal paths. One signal path is delayed by the amount of time equal to a whole multiple of the complex waveform period.

A phase detector maintains phase and also acts to isolate the noise from the signal. The isolated noise is subtracted from the combined input signal resulting in an artifact-free output.

In a second embodiment, no time delay occurs, and the real time signal is phase detected with an ECG waveform retrieved in synchronization with the real time signal from memory, isolating the noise thereto. The isolated noise is then subtracted from the real time signal and stored signal.

The foregoing features of the present invention may be more fully understood from the following detailed discussion of a specific illustrative embodiment thereof, presented hereinbelow in conjunction with the accompanying drawing, in which.

DETAILED DESCRIPTION OF THE INVENTION

Briefly in overview, it is a fundamental aspect of the present invention that noise and artifacts can be removed from a repeating complex signal due to the fact that the noise and artifacts are essentially non-repeating or repeat with a different period than the desired source waveform. The repeating complex waveform is phase-locked in a manner that isolates those signal segments (noise and artifacts) that do not intrinsically repeat with the waveform. The isolated artifacts are then removed from a combined complex waveform in manner more fully discussed below, providing a mostly artifact-free ECG signal.

Figure 1:
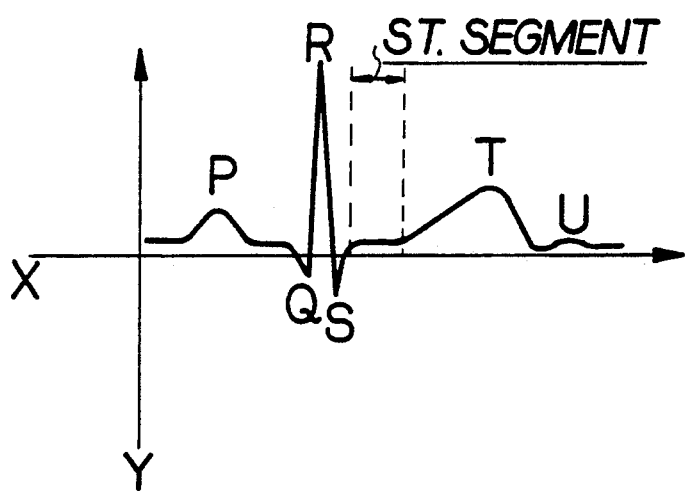
FIG. 1 is a real time ECG signal representation.

With this in mind, and referring to FIG. 1, a detailed diagram of a typical electrocardiogram or ECG signal is shown. Only the portion of this signal that is associated with a single heartbeat is provided and this represents the repeating complex waveform that is the subject to the signal processing of the present invention. As shown in FIG. 1, an ECG can be conceptually broken down into a sequence of characteristic segments the sum of which form the complex waveform of FIG. 1. As discussed above, proper medical diagnosis requires a clear picture of slight changes in these characteristic segments. Although these individual segments are of primary concern to the cardiologist, the present invention operates on the complex waveform as a whole and not the individual segments alone.

Figure 2A:
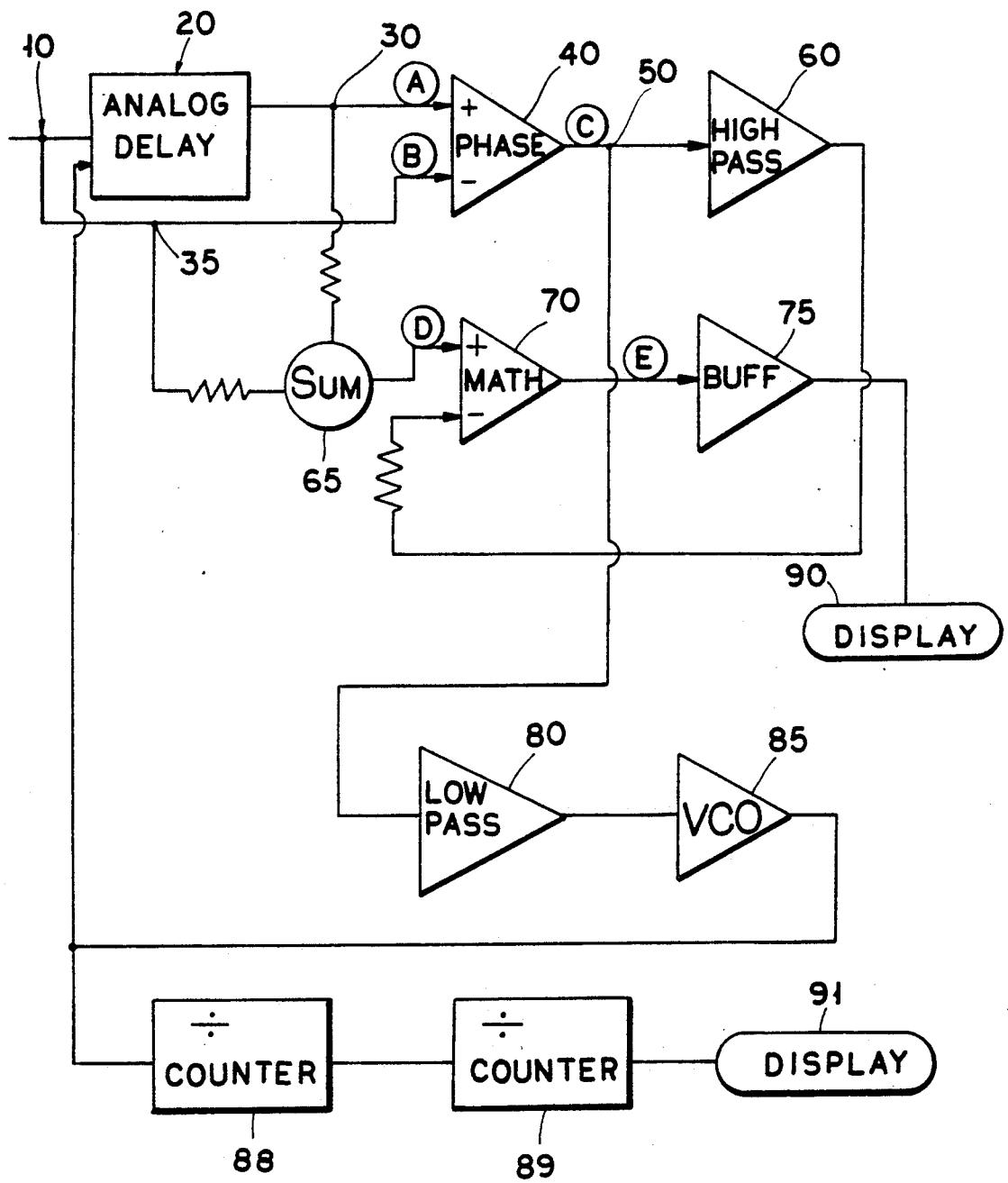
FIG. 2a is a block diagram of one embodiment of the present invention.
Figure 3A:
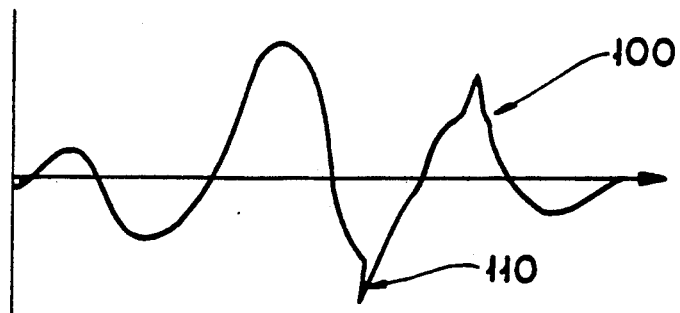
FIGS. 3a-d provides a series of ECG signal representations taken at various points of signal processing, as is more fully discussed hereinbelow.

This is more clearly shown in FIG. 2a which provides a schematic block diagram of the operative system of the present invention. Referring now to FIG. 2a, the input ECG signal is taken from a heart sensor or similar (not shown) forming an input to node 10. This input is then split into two separate signal paths providing two real time carriers of the sensed ECG. The first signal path is directed to analog delay circuit 20. Circuit 20 operates to time delay the real time ECG signal by an amount of time associated with one heartbeat, i.e., one period of the complex waveform of FIG. 1. Although this discussion assumes a single period delay this is by no means a limitation; in fact it is equally likely that the delay by circuit 20 is set at some whole multiple of this period and the only intrinsic limitation is that the time delay is such that the delayed signal path remains in phase with the undelayed portion of the signal as will become more clear from the following discussion. The resulting signal from circuit 20 is divided into two branches at node 30. A sample signal at point (A) in FIG. 2a is shown in FIG. 3a.

Figure 3B:
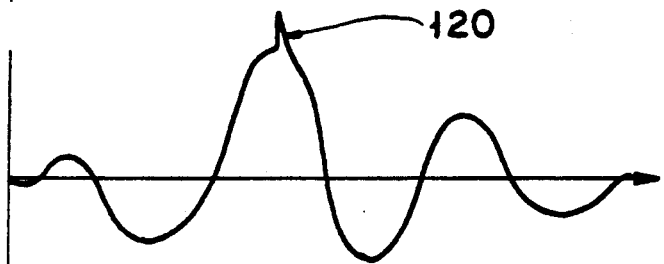

The real time ECG signal is also divided, this at node 35 in FIG. 2a with the two branches directed to phase detector 40 and summing node 65 respectively. The real time signal, a sample of which is depicted in FIG. 3b as taken from point (B) in FIG. 2a, is combined at detector 40 with the delayed signal path, forming output (C) to node 50. It should be noted that although a real time signal path is used, this is for illustration only and that the system only requires that the two signal paths from nodes 30 and 35 feeding detector 40 be time displaced and in phase for proper operation.

During in-phase operation of the phase detector 40, the output of node 50 will contain essentially only the artifacts from the two inputs to the detector. These artifacts are predominantly high frequency signals which pass through high pass filter 60. The passband for filter 60 can be adjusted according to the types of artifacts being encountered. The output of filter 60 is then inputted on the negative terminal of math amp 70.

Figure 3C:
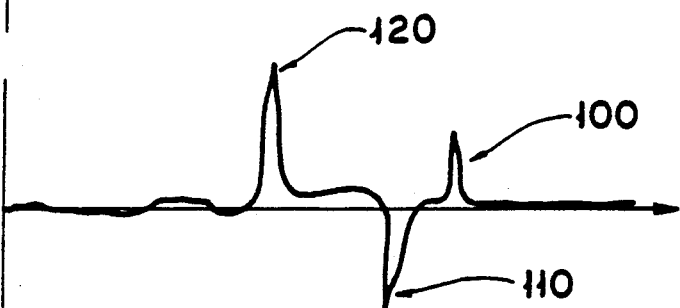
Figure 3D:
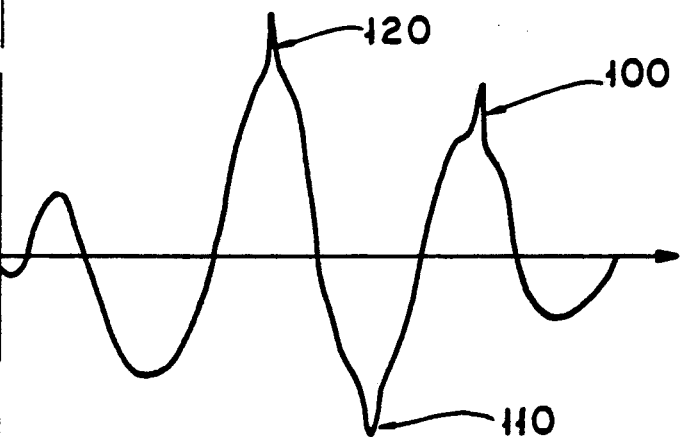

The real time signal path from node 35 and delayed signal path taken from node 30 are summed at summing node 65. This provides the second input to math amp 70 inputted at the positive terminal. A sample input (D) to the positive terminal of math amp is shown in FIG. 3d as the sum of the waveforms depicted in FIGS. 3a and 3b. The output of math amp 70 forms the ECG waveform without the distorting artifacts. This output is then buffered by amp 75 forming the final clean ECG for display 90.

The above description has assumed in-phase operation, which is provided for by the following. Node 50 carries the output of detector 40 to low pass filter 80 which in turn feeds voltage controlled oscillator 85. During in-phase operation, the signal (C) will comprise only high frequency noise which is removed by lowpass filter 80. If the delayed and undelayed signal paths drift out of phase, phase detector 40 will generate an output with low frequency component representative of the out of phase condition. This component will pass through filter 80 and actuate voltage controlled oscillator ("VCO") 85 which in turn generates a corrective beat frequency to delay circuit 10, bringing the respective signals back into phase. In addition, since the VCO is by definition timed at some multiple to the frequency of the heartbeat, it can be processed by serial counters (dividers) 88 and 89 to output a signal representative of heart rate as shown by display 91.

Figure 2B:
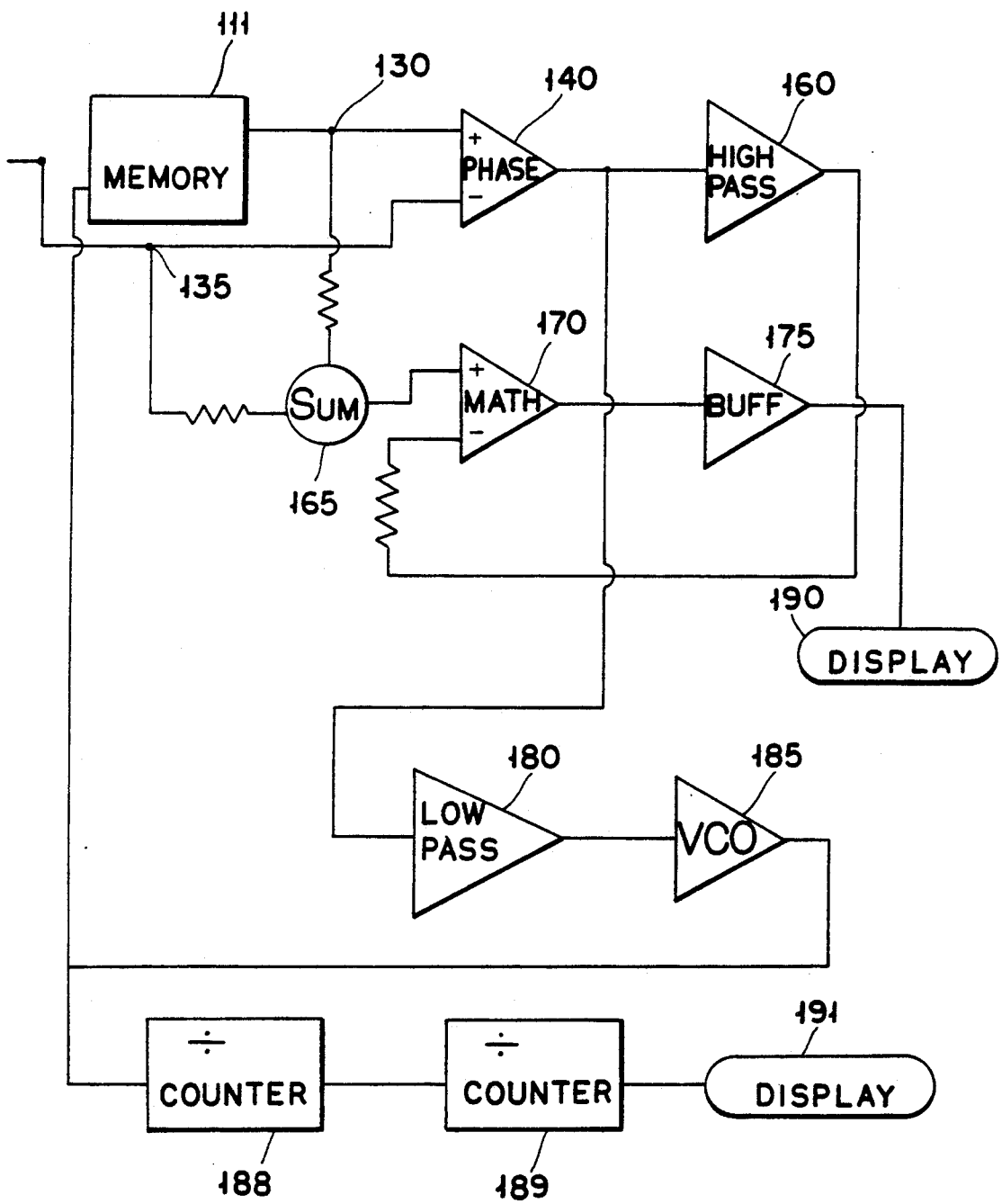
FIG. 2b is a block diagram for a related, second embodiment of the present invention.

A second embodiment of the present invention involves substituting a stored ECG waveform in place of the delayed ECG waveform. More particularly, in FIG. 2b, instead of analog delay, the system would employ memory device 111 containing a stored ECG waveform for a particular patient. Output from memory 111 would be a continuous signal repeating the stored complex ECG waveform in phase with the currently measured ECG waveform. In phase operation is maintained by VCO 185, operated to control output of memory 111, pursuant to phase discrepancies detected upstream by detector 140. The stored ECG signal would be in phase with the received ECG signal and signal processing would proceed as described above The remaining component means of FIG. 2b are equivalent to those in FIG. 2a, except that the reference characters in FIG. 2b are placed in a 100 series of numbers, e.g., the counters 88 and 89 in FIG. 2a are designated 188 and 189 in FIG. 2b.

In practice, the present invention operates in conjunction with conventional sensors and signal processors. For example and referring now to FIGS. a-e, a delayed signal FIG. 3a contains the characteristic waveform of an ECG signal with artifacts 100 and 110. A second real time ECG signal contains the same characteristic waveform, but with artifacts 120. When these two waveforms are combined in detector 40 and are in-phase, the characteristic waveforms cancel out, leaving only the artifacts 100, 110 and 120 as shown in FIG. 3c.

Figure 3E:
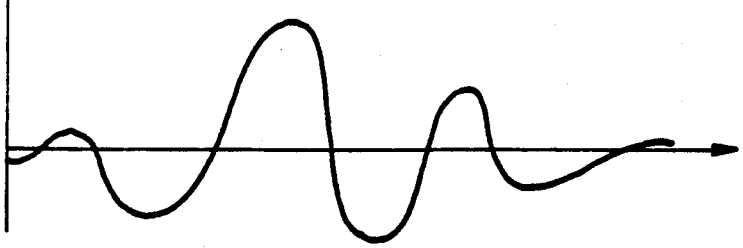

Concurrent therewith, the delayed and undelayed signal paths including all artifacts, are summed at summing node 65 forming an enlarged amplitude signal as reflected in FIG. 3d, again with the artifacts as indicated. The associated artifacts are then removed by combining the signal shown in FIG. 3c with the signal shown in FIG. 3d, which then provides the artifact-free ECG as shown in FIG. 3e as the output of math amp 70.

The above-described arrangement is merely illustrative of the principles of the present invention. Numerous modifications and adaptations thereof will be readily apparent to those skilled in the art without departing from the spirit and scope of the present invention.

What is claimed is:

1. In a system for removing artifacts from a repeating complex waveform comprising a signal input and divider means for receiving an electrical signal containing said complex waveform and dividing said input signal into plural signal paths; signal delay means for time delaying said signal of at least one of said plural signal paths by an amount substantially equal to a period of one or a whole multiple of said complex waveform; artifact isolation means for isolating an artifact containing component signals from said delayed signal path and a second path, wherein said component signal of second signal path is time displaced from said signal of said delayed signal path; summing means for forming a combined signal by summing said signal from said delayed signal path with said signal of at least said second signal path; artifact removal means for subtracting said isolated artifact containing component from said combined signal thereby forming an essentially artifact-free signal; and output means for transmitting said artifact-free signal to an output device.

2. The system of claim 1 wherein said signal delay means is an analog delay circuit connected with a voltage controlled oscillator for phase feedback control.

3. The system of claim 2 wherein said voltage control oscillator received phasing signal input from a phase detector means of said delayed and second signals.

4. The system of claim 3 wherein said phase detector means comprising a low pass filter means and produces a phase controlling output when said delayed and second signals fall out of phase.

5. The system of claim 1 wherein said artifact isolation means comprises a high pass filter means between a phase detector means and a math amp negative terminal.

6. The system of claim 1 further comprising output means for display of artifact-free complex waveforms as received from said artifact removal means.

7. A method for removing artifacts from an electrocardiogram (ECG) comprising the steps of:
  receiving and dividing an ECG input signal of at least one heartbeat into at least two signal paths;
  delaying at least one of said signal paths by an amount substantially equal to the period of the ECG associated with one heartbeat;
  isolating said artifacts from said delayed signal path and a second signal path time displaced from said delayed signal path;
  combining said signal paths from which said artifacts have been isolated;
  subtracting from said combined signal paths said isolated artifacts; and
  outputting a signal representative of said ECG but essentially free from artifacts.

8. The method of claim 7 wherein said delaying step comprises maintaining phase between the delayed signal path and second signal path.

9. The method of claim 8 further comprising the step of outputting a delayed or stored signal representative of a frequency of the heartbeat.

10. In combination in an apparatus for the processing of an ECG signal comprising means for receiving a signal representative of a patient's ECG; means for storing a portion of said received signal representative of one heartbeat; means for receiving and inputting a real time ECG signal; means for isolating artifacts from a real time ECG signal and from said stored ECG signal; means for maintaining phase between said real time ECG signal and said stored ECG signal; summing means for combining said real time ECG signal and said stored ECG signal; subtraction means for removing said isolated artifacts from said combined signals; and output means for outputting an ECG signal essentially free of artifacts.

11. In the apparatus of claim 10 wherein the phase maintenance means includes a frequency detection means for determining a heart rate from said real time ECG signal.

12. In the apparatus of claim 11 wherein said phase maintenance means which includes a phase detector means, a low pass filter means and a voltage controlled oscillator is further connected to and controlling the output of said storing means.

* * * * *